United States Patent [19]

Nogimori et al.

[11] Patent Number: 4,609,549
[45] Date of Patent: Sep. 2, 1986

[54] BIOLOGICALLY ACTIVE SUBSTANCE FROM ISLETS-ACTIVATING PROTEIN

[75] Inventors: Katsumi Nogimori; Makoto Tamura; Shigeki Kurokawa; Motoyuki Yajima, all of Ohtsu, Japan

[73] Assignee: Kaken Pharmaceutical Co., Ltd., Tokyo, Japan

[21] Appl. No.: 606,479

[22] Filed: May 3, 1984

[30] Foreign Application Priority Data

May 11, 1983 [JP] Japan .................................. 58-82363

[51] Int. Cl.⁴ ..................... C07K 15/04; A61K 37/02; A61K 39/10; A61K 37/43
[52] U.S. Cl. ........................................ 424/92; 435/68; 530/350; 530/825
[58] Field of Search ........................... 435/68; 424/92; 260/112 R

[56] References Cited

U.S. PATENT DOCUMENTS 3,983,229  9/1976  Relyveld ................................. 424/92
4,455,297  6/1984  Syukuda et al. ....................... 424/92

FOREIGN PATENT DOCUMENTS 1569046  6/1980  Japan .

*Primary Examiner*—Howard E. Schain
*Attorney, Agent, or Firm*—Oblon, Fisher, Spivak, McClelland & Maier

[57] ABSTRACT

The present invention relates to biologically active substances obtained by reacting Islets-Activating Protein having an insulin secretion promoting action with a carbonyl compound in the presence of a reducing agent; to anti-diabetic composition in dosage unit form comprising the substance of the present invention; to pertussis vaccine in dosage unit form comprising the substance of the present invention; and to a process for the preparation of the same. The substances of the present invention are suppressed in leukocytosis-promoting effect.

11 Claims, No Drawings

BIOLOGICALLY ACTIVE SUBSTANCE FROM ISLETS-ACTIVATING PROTEIN

The present invention relates to a biologically active substance obtaited by reacting Islets-Activating Protein having an insulin secretion promoting action with a carbonyl compound in the presence of a reducing agent, to a pharmaceutical composition containing the same and to a process for the preparation of the same.

As a prior art, Japanese Patent Application Laying Open Nos. 96392/78 (Application No. 10397/77) and 136592/78 (Application No. 49641/77) disclose biologically active substances having an insulin secretion promoting action obtained by the cultivation of suitable strain(s) of the microorganism Bordetella pertussis (Phase I or II) in a suitable culture medium or media and a pharmaceutical composition for use in an antidiabetic comprising the same. Further, Japanese Patent Application Laying Open No. 67591/82 (Application No. 142323/80) and No. 67592/82 (Application No. 142324/80) disclose proteinic components in a biological active substance having an insulin secretion promoting action obtained by the cultivation of suitable strain(s) of the microorganism Bordetella pertussis (Phase I or II) in a suitable culture medium or media and further, disclose resembled substances of the proteinic components.

The present invention relates to modified substance prepared from the biological active substances mentioned above, that is Islets-Activating Protein. The modified substance of the present invention is more suppressed in leukocytosis-promoting effect than that of the non-modified Islets-Activating Protein, while maintaining an insulin secretion promoting action.

It is an object of the present invention to provide a biologically active substance obtained by reacting Islets-Activating Protein having an insulin secretion promoting action with a carbonyl compound of the formula

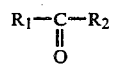

wherein $R_1$ is hydrogen atom, methyl group or

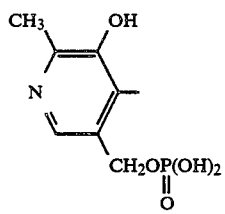

group and $R_2$ is hydrogen atom or alkyl group of 1 to 3 carbon atoms, in the presence of a reducing agent.

Another object of the present invention is to provide anti-diabetic composition and a pertussis vaccine in dosage unit form comprising a therapeutically effective amount of a biologically active substance prepared from Islets-Activating Protein and a pharmaceutically acceptable carrier.

Other object of the present invention is to provide a process for preparing a biologically active substance, comprising reacting Islets-Activating Protein having an insulin secretion promoting action with a carbonyl compound of the formula

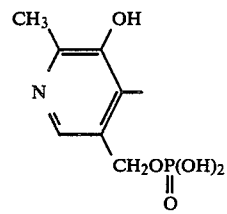

wherein $R_1$ is hydrogen atom, methyl group or

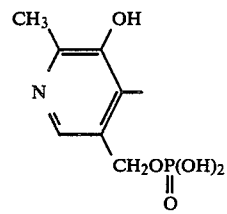

group and $R_2$ is hydrogen atom or alkyl group of 1 to 3 carbon atoms, in the presence of a reducing agent at a temperature of 0° to 40° C. for 5 minutes to 24 hours.

The other objects of the present invention will become apparent from a consideration of the following descriptions.

The substance of the present invention is prepared from Islets-Activating Protein (hereinafter abbreviated and referred to as "IAP"). IAP is obtained by the cultivation of suitable strain(s) of the microorganism Bordetella pertusiss (Phase I or II) in suitable medium or media. The representative IAPs have the following properties:

a molecular weight of 73,000±11,000 as determined by gel filtration;

a protein content as determined by Lowry's method being not less than 95% by weight;

a glucide content by the phenol-$H_2SO_4$ method being less than 2% by weight;

the lipid content being lower than the limit of detection;

percentile amino acid composition of the protein moiety (average ratio, $\mu M/100 \mu M$) being: aspartic acid, 7.5–7.9; threonine, 6.8–7.8; serine, 5.9–7.6; glutamic acid, 8.8–10.0; proline 5.5–6.4; glycine, 8.7–9.6; alanine, 9.0–10.8; cystine/2, 1.0–2.5; valine, 6.5–7.6; methionine, 2.5–3.3; isoleucine, 3.6–4.6; leucine, 7.4–8.7; tyrosine, 5.1–6.8; phenylalanine, 3.7–4.5; lysine, 3.1–4.4; histidine, 0.9–1.5; and arginine, 6.1–6.6;

disc electrophoretic pattern; acrylamide (polyacrylamide concentration, 7.5%; a 1N KOH-glacial acetic acid buffer (pH 4.3)) disc electrophoresis of said substance giving a very sharp single band on the cathode side;

hydroxyapatite column chromatographic pattern: said substance in 0.1M phosphate buffer (pH 7.0) being adsorbed on said column and the adsorbed substance being eluted with 0.1M phosphate buffer (pH 7.0) containing 0.5M NaCl;

isoelectric point of pH 8.9±0.5; and optical rotation $[\alpha]_D^{25} = -29° \pm 5°$.

The substance of the present invention can be produced by reacting IAP with a carbonyl compound represented by the formula:

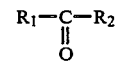

(wherein $R_1$ and $R_2$ are the same defined as above) in the presence of a reducing agent, thereby introducing an alkyl group represented by the formula:

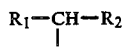

(wherein $R_1$ and $R_2$ are as defined above) or a substituted pyridylmethyl group represented by the following formula:

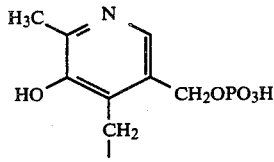

into the free amino groups in IAP.

As a reducing agent used in the present invention for instance, sodium borohydride, sodium cyanoborohydride, or a complex of borane and heterocyclic compound of nitrogen such as pyridine and morpholine, or amine compound such as dimethylamine and triethylamine may be mentioned.

Some of the advantageous reaction conditions for modifying IAP are shown below.
1. PH of the reaction system: 6 to 10, preferably 7 to 9.
2. Reaction solvent: 0.05–0.5M, preferably 0.1M phosphate buffer solution.
3 IAP concentration: 0.01 to 1% by weight.
4 Carbonyl compound concentration: 5 to 100 mM.
5. Reducing agent concentration: 5 to 100 mM.
6. Reaction temperature: 0° to 40° C.
7. Reaction time: 5 minutes to 24 hours.

The substances of the present invention are specified in that 4 to 95%, preferably 50 to 95%, of the free amino groups per one molecule of IAP are modified by the reaction with a carbonyl compound in the presence of a reducing agent. The substance of the present invention are suppressed in leukocytosis-promoting effect while maintaining an equal hyperglycemia inhibitory action substantially equal to the non-modified IAP.

Further, the substances of the present invention can be utilized for a pertussis vaccine. IAP (or N-IAP) is one of the pertussis infection preventive antigen but it can not be immediately used as an effective pertussis vaccine because of the side effects such as leukocytosis-promoting effect. It is therefore necessary that IAP is processed into a toxoid by a formalin or glutaraldehyde treatment. The modified IAP of the present invention almost suppresses the side effects such as leukocyte increasing action and it has been ascertained that this substance has an effective infection preventive action without toxoid processing.

Hereinbelow, one of the purification methods, one of the modification rate determining methods, one of the electrophoresis methods, one of the activity measuring methods for the product according to the present invention will be described in detail.

I. Purification method 2 to 3 mg of the reaction product is subjected to gel filtration with a column (1.5×95 cm) of Sephacryl S-200 (Pharmacia Fine Chemicals) using a 0.1M phosphate buffer solution (pH 7.0, containing 2M of urea) as effluent. The protein content of each fraction is measured by Lowry et al method using bovine serum albumin as standard protein.

II. Determination of modification rate

A purified sample of each of non-modified IAP (control) and the substance of the present invention is dissolved in distilled water (500 μg/ml). To 400 μl of this aqueous solution are added 400 μl of 0.1% trinitrobenzenesulfonic acid and 4% $NaHCO_3$ (pH 9.0), and the mixture is reacted at 37° C. for 2 hours, then added with 400 μl of 10% SDS, allowed to stand at 37° C. for 10 minutes and further added with 400 μl of 1N HCl. The absorbance at 335 nm is measured by a spectrometer (139 HITACHI UV-Vis spectrophotometer). The modification rate is determined by calculating the absorbance of the modified IAP derivative in percentage to the absorbance of the non-modified IAP (given as 100%).

III. Polyacrylamide gel disc electrophoresis

The purity of the substance of the present invention can be determined by disc electrophoresis of polyacrylamide gel (polyacrylamide concentration, 7.5%; 1N KOH-acetate buffer (pH 4.3)). The electrophoresis is conducted by using 30 μg of sample (in terms of protein quantity) per piece of gel at a current flow of 4 mA for 2 hours. The sample is stained with Amide Black 10B and decolorized with a 7.5% acetic acid solution.

IV. Epinephrine hyperglycemia inhibitory activity (EpI activity)

Each sample is intravenously injected to the male Wistar rats (about 150 g body weight) at a dose of 12 μg/kg, and after sample injection, epinephrine is subcutaneously injected to the rats under fast on a daily basis. The difference between blood sugar level before epinephrine injection and that one hour after injection is compared with the difference in the control group to thereby determine the EpI activity (%).

$\Delta G_C$: control group [(blood sugar level after epinephrine injection)−(blood sugar level before injection)]

$\Delta G_T$: sample-administered group [(blood sugar level after epinephrine injection)−(blood sugar level before injection)]

$$EpI \text{ activity } (\%) = \frac{\Delta G_C - \Delta G_T}{\Delta G_C} \times 100$$

V. Leukocytosis-promoting activity (ΔLP activity)

Each sample is intravenously injected into male Wister rats (about 150 g body weight) at a rate of 12 μg/kg, and the leukocyte count is measured on a daily basis. The leukocyte increment is determined from the difference in leukocyte count between the sample-administered group and the control group.

ΔLP activity=(leukocyte count in sample-administered group)−(leukocyte count in control group)

VI Preparation and purification of IAP

IAP may be prepared by the methods disclosed in Japanese Patent Application Laying Open Nos. 96392/78, 136592/78 and 67591/82.

A detailed description of the preparation of IAP and the properties of IAP are given below.

IAP having an activity of promoting the secretion of insulin is a substance which can be obtained by culturing the microorganism of *Bordetella pertussis* (Phase I or Phase II), most preferably *Bordetella pertussis* (Phase I) in a solid or liquid culture medium and after collecting crude product from the cultured bacterial cells and/or the culture medium, purifying the thus obtained crude product.

Collection and purification of the crude product to obtain IAP from the culture can be accomplished in general by one or combination of the methods of column chromatography, dialysis, electrophoresis, gel-filtration, ion-exchange, fractional precipitation, extraction with solvent and molecular sieve, and accordingly, the present invention is not defined by any specific methods for collection and purification.

As an example of the highly advantageous methods for collecting and purifying the crude product to obtain IAP, a column chromatographic process is suggested as shown below. According to this process, the supernatant of the culture medium of the bacteria is passed through a column filled with Hydroxyapatite column, Haptoglobin Sepharose column, Carboxymethyl Sepharose column such as Carboxymethyl Sepharose CL-6B column (made by Pharmacia Fine Chemicals. Inc.), Sephacryl (S-200) column, Concanavalin Sepharose column such as Con A-Sepharose column (made by Pharmacia Fine Chemicals. Inc.), Biogel (P-100) column, Biogel (P-150) column, p-Acetoxymercurianiline Sepharose column such as p-Acetoxymercurianiline Sepharose 6 MB column or Anti-IAP antibody-Sepharose column such as Anti-IAP antibody-Sepharose 4B column to adsorb IAP. The adsorbed IAP is eluted from the column-material with a suitably selected elutant such as aqueous Tris-hydrochloric acid solution containing KSCN, aqueous phosphate buffer solution containing urea, or aqueous phosphate buffer containing sodium chloride. By applying dialysis to the eluted solution, unnecessary salts are removed to obtain a fraction containing IAP.

Since IAP is also present in the cultured bacterial cells, according to the necessity, IAP may be collected therefrom by, for example, adding sodium chloride to the aqueous suspension of the cells to leach out IAP into the aqueous solution.

The so-called precipitation method by ammonium sulfate popularly used in the art is also applicable for preparation of IAP. In this case, solid ammonium sulfate is added to the supernatant of the culture medium of the bacteria to a point approximate to saturation and the pH of the mixture is adjusted to 6 to 7 with a dilute ammonia liquor. Then, the thus obtained precipitate is separated and washed with water, and then IAP is extracted with aqueous 0.1M tris-buffer solution of pH 8 containing sodium chloride at 0.5M to obtain a solution of IAP.

Although *Bordetella pertussis* produces IAP as has been described above, its various mutants obtained by the conventional method for causing mutation of the bacteria, such as modification of the components of culture medium, exposure of the bacteria to a high energy radiation such as ultraviolet rays, X-rays, etc. or the use of a mutagenic agent, are also useful as a microorganism for producing IAP.

In addition, although the liquid-shaking culture method is preferable from the viewpoints of the yield of IAP and its activity, other methods for culturing may be used.

The mycological properties of and conditions for culturing the bacterial species belonging to the genus Bordetella are described in "Bergy's Manual of Determinative Bacteriology, 8th Ed.", (1974), Williams & Wilkins Co., Baltimore, Md., USA., "J. Exp. Med." Vol. 129, pages 523–550 (1969) and "Saikingaku Jisshu Teiyo (Handbook for Mycological Training) 3rd Ed." (1972), Maruzen Co.

The chemical and physical properties of IAP are described below.

The powder of IAP obtained by freeze-drying the aqueous dialysed and de-salted solution is non-deliquescent, and white or light brown in colour, and is soluble in water to the extent of 3 to 5 mg/ml at room temperature. It is also soluble in pyridine, 2-mercaptoethanol and aqueous solution of sodium dodecylsulfate and of cystine. When IAP is put into aqueous 6N hydrochloric acid solution, a precipitate white in colour separates out. Addition of sodium sulfate, dry ice plus acetone, ethanol, trichloroacetic acid, aqueous solution of zinc chloride, or aqueous solutions containing several other kinds of metal ions to an aqueous solution of IAP at 4° C., causes the aqueous solution to become turbid and a precipitate to settle out. When IAP is put into a mixture of water and chloroform or of water and n-butanol, IAP gathers on the interface of both liquids.

When an aqueous solution of IAP is heated to 80° C. or higher, the solution becomes turbid white in colour. In addition, when IAP is dissolved into aqueous 0.1M phosphate buffer solution of pH of 7.0 containing sodium chloride at 0.5M and the solution is subjected to dialysis against distilled water as the external liquid, the mixed solution becomes turbid once, however, with the progress of dialysis, the white turbidity disappears completely.

Molecular weight of IAP:

(i) The molecular weight of IAP determined by gel-filtration method using a column (2.8 cm×80 cm) of Biogel P-100 (made by Bio. Rad. Co.) equilibrated by aqueous 0.1M phosphate buffer solution containing sodium chloride at 0.5M is 73,000±11,000.

(ii) After dissolving the active substance of the present invention into aqueous 0.01M potassium dihydrogen phosphate buffer solution additionally containing 0.1M of sodium chloride and 2M of urea, the solution is subjected to an "Hitachi-ultracentrifuge for Analysis Model UCA-1" (made by Hitachi Works Co., Ltd. Japan) of 60,000 r.p.m. at 15° C. to obtain the molecular weight.

The thus obtained molecular weight of IAP determined by ultracentrifugal method is 116,000±7,000.

(iii) IAP is treated by slab-type SDS-polyacrylamide-disc electrophoresis (Laemmli's method: Laemmli, U.K. (1970) Nature (London) 227, 680–685) in which IAP is subjected to 16-hour electrophoresis by using acrylamide gel with a density gradient of 10–30% under the following conditions: acrylamide gel crosslinking ratio=37:1, concentrated gel pH=6.8, migrating gel pH=8.8, and electrophoresis voltage=90 V. Then the resultant IAP is treated with 20% TCA for one hour and then stained with Coomassie Blue. For converting protein into SDS, the treated IAP is treated with 1% SDS at 100° C. for 5 minutes. The molecular weight of IAP as determined by SDS-gel electrophoresis is 105,700±5,000.

Component of IAP:

The content of protein in IAP determined by Lowry's method is not less than 95% by weight, and the content of glucide determined by phenol-sulfuric acid method is less than 2% by weight. The concentration of lipid in IAP is below the lower limit of detection.

The following literatures are referred to for measurement of the respective components:

Protein: Lowry, O. H., N. J. Rosebrough, A. L. Farr and R. J. Randall: "J. Biol. Chem.", 193: 265, 1951.

Glucide: Phenol-$H_2SO_4$ method. Dobois, M., K. A. Giles, J. K. Hamilton, P. A. Rebers and F. Smith: "Anal. Chem.", 28 350, 1956.

Lipid: Total lipid and lipid conjugate are measured according to Marsh and Weinstein method (J. B. Marsh and D. B. Weinstein: "J. Lipid Res.", 7,574, 1966) by extracting the material before and after hydrolysis into chloroform, chloroform-methanol and heptane.

The amino acid composition of the protein component of IAP is determined according to Lowry, O. H. et al. "J. Biol. Chem.", 193 page 265 (1951), the result being as follows: (IAP is hydrolyzed in aqueous 6N hydrochloric acid at 110° C. for 24 hours at a concentration of $\mu M/100 \mu M$).

Compositional ratio is aspartic acid of 7.5 to 7.9; threonine of 6.8 to 7.8; serine of 5.9 to 7.6; glutamic acid of 8.8 to 10.0; proline of 5.5 to 6.4; glycine of 8.7 to 9.6; alanine of 9.0 to 10.8; cystine/2 of 1.0 to 2.5; valine of 6.5 to 7.6; methionine of 2.5 to 3.3; isoleucine of 3.6 to 4.6; leucine of 7.4 to 8.7; tyrosine of 5.1 to 6.8; phenylalanine of 3.7 to 4.5; lysine of 3.1 to 4.4; histidine of 0.9 to 1.5 and arginine of 6.1 to 6.6.

Isoelectric point of IAP:

The isoelectric point of IAP determined by the method described in Wringley, C.W., "J. Chromatogr.", 36, 362–372 (1968) is pH 8.9±0.5.

Optical rotation of IAP:

The optical rotation is $[\alpha]_D^{25} = -29 \pm 5°$.

Absorption of ultraviolet of IAP:

The absorption of ultraviolet is $\lambda_{max}$ 277±3 nm (log $\epsilon$ 4.79±0.3).

Nuclear magnetic resonance spectrum of IAP:

The specific absorptions of nuclear magnetic resonance spectrum are 1.2–3.5 ppm, 4.0–6.0 ppm and 6.7–8.8 ppm.

Sedimentation constant of IAP:

The sedimentation constant is 6.5±0.3S.

Elemental Analysis of IAP (Found):

Carbon content is 46.6±6.2%, hydrogen content is 6.7±0.9%, nitrogen content is 14.4±1.2%, sulfur content is 1.7±0.4% and oxygen content is balance.

Biological properties of IAP:

IAP has an activity of promoting the secretion of insulin not less than 193 unit/$\mu$g and an activity of improving the glucose tolerance in mammals, and these actions are maintained for several weeks to several months after a single administration of IAP.

Acute toxicity ($LD_{50}$, i.v.) to ddY mice is about 230 $\mu$g/kg body weight.

The present invention will be explained more in detail while referring to the following non-limitative examples.

EXAMPLE 1

In a vessel, 4 mg of IAP was dissolved in 2 ml of a 0.1M phosphate buffer solution (pH 7.0) containing 2M urea, and to this solution was added 3 $\mu$l of a pyridine-borane complex dissolved in 0.1 ml of methanol (final concentration 15 mM). The mixed solution was further added with formaldehyde (10 $\mu$l of a 29.4 times diluted solution of 37% formalin) and reacted at room temperature (20°–25° C.) for 2 hours. The reaction was stopped by adding 1M glycine (0.5 ml), and the reaction solution was dialyzed against distilled water by using a cellulose tube to remove the reagents and further subjected to gel filtration with a Sephacryl S-200 column to obtain 3.8 mg of a reductive methylation product of IAP (modification rate 92%) as an IAP derivative. The obtained IAP derivative showed a single band in the disc electrophoresis.

EXAMPLES 2–10

By following the procedure of Example 1 but by changing the reducing agent (sodium borohydride, sodium cyanoborohydride or pyridine-borane complex) and the kind and/or concentration of carbonyl compound, there were produced various kinds of modified IAP derivative. The reaction conditions, modification rate and yield are shown in Table 1.

TABLE 1

|  | IAP wt (mg) | Buffer (pH) | Reducing agent (mM) | Carbonyl compound (mM) | Reaction time (hr) | Modification rate (%) | Yield (mg) |
| --- | --- | --- | --- | --- | --- | --- | --- |
| Example 2 | 4 | 7.0 | Pyridine-borane 15 | Formaldehyde 10 | 4 | 88 | 3.9 |
| Example 3 | 4 | 8.0 | Pyridine-borane 15 | Formaldehyde 40 | 2 | 91 | 3.7 |
| Example 4 | 0.8 | 7.0 | Pyridine-borane 15 | Acetaldehyde 10 | 2 | 42 | 0.7 |
| Example 5 | 0.8 | 7.0 | Pyridine-borane 15 | Acetaldehyde 40 | 2 | 58 | 0.7 |
| Example 6 | 1 | 8.0 | Sodium cyanoborohydride 15 | Formaldehyde 20 | 1 | 89 | 0.8 |
| Example 7 | 0.8 | 7.0 | Pyridine-borane 20 | Acetone 40 | 2 | 12 | 0.7 |
| Example 8 | 0.8 | 9.0 | Pyridine-borane 15 | Acetone 40 | 2 | 22 | 0.7 |
| Example 9 | 1.0 | 8.0 | Sodium borohydride 50 | Pyridoxalphosphoric acid 5 | 1 | 38 | 0.7 |
| Example 10 | 1.0 | 7.0 | Pyridine-borane 15 | Propionaldehyde 40 | 2 | 45 | 0.9 |

EXPERIMENTAL TEST 1

The pharmacological activity, acute toxicity, and stability in an alkaline solution, of the resultant products obtained in the Examples were examined in the manners described above.

(i) Pharmacological activity:

The modified IAP obtained in Examples 1–10 were administered to the male Wistar rats at a dose of 12 μg/kg, respectively and their in vivo activities (EpI activity and ΔLP activity) one day after the administration were examined, the results being shown in Table 2. The control is non-modified IAP.

|  | EpI activity (%) | ΔLP activity ($\times 10^2/mm^3$) |
|---|---|---|
| Example 1 | 84.0 | 0 |
| Example 2 | 86.0 | 0 |
| Example 3 | 83.5 | 0 |
| Example 4 | 81.5 | 42.9 |
| Example 5 | 82.0 | 38.7 |
| Example 6 | 82.4 | 5.0 |
| Example 7 | 79.6 | 72.5 |
| Example 8 | 73.5 | 69.8 |
| Example 9 | 82.1 | 16.5 |
| Example 10 | 80.2 | 54.6 |
| Control | 85.0 | 140.1 |

(ii) Acute toxicity:

The acute toxicity ($LD_{50}$) of the modified IAP obtained in Examples 1, 3, 4, 9 and 10 was examined by intravenously injecting some of the modified IAP to the ddY mice (male), the results being shown in Table 3. It was found that $LD_{50}$ of the modified IAP of the present invention was either equal to or higher than that of non-modified IAP. The control is non-modified IAP.

TABLE 3

|  | $LD_{50}$ (μg/kg) |
|---|---|
| Example 1 | 250 |
| Example 3 | 232 |
| Example 4 | 215 |
| Example 9 | 240 |
| Example 10 | 236 |
| Control | 215 |

(iii) Stability:

The stability in an amine-containing alkaline solution of the modified IAP of the present invention and an IAP amidino derivative disclosed in Japanese Patent Application Laid-Open No. 129295/80 (Application No. 35877/79) was examined. The results are shown in Table 4.

Table 4 shows the change with time of the EpI activity and ΔLP activity of the reductively methylated IAP obtained in Example 1 of the present invention, the acetamidinated IAP obtained in Preparation Example 1 of Japanese Patent Application Laying Open No. 129295/80 and the non-modified IAP, as measured in 3.44M methylamine solution (pH 9.5). The results show that the modified IAP of the present invention is more stable than the acetamidino-incorporated IAP in the methylamine solution.

TABLE 4

| Treatment time (hr) | The present invention (reductively methylated IAP) EpI activity (%) | ΔLP activity ($\times 10^2/mm^3$) | Comparative example (acetamidinated IAP) EpI activity (%) | ΔLP activity ($\times 10^2/mm^3$) | Control (non-modified IAP) EpI activity (%) | ΔLP activity ($\times 10^2/mm^3$) |
|---|---|---|---|---|---|---|
| 0 | 83.5 | 0 | 81.5 | 0 | 82.0 | 144 |
| 24 | 82.0 | 0 | 80.2 | 4 | 83.0 | 141 |
| 48 | 82.5 | 0 | 76.5 | 12 | 80.5 | 138 |
| 72 | 79.8 | 0 | 75.4 | 27 | 79.8 | 139 |

EXPERIMENTAL TEST 2

(i) The reductively methylated IAP of the present invention was prepared according to the procedure of Example 1.

(ii) The IAP processed into toxoid with glutaraldehyde (hereinafter referred to as toxoid-processed IAP) used as the comparative example was prepared in the following precedures. To 0.1M phosphate buffer solution (containing 2M urea, pH 7.0) containing IAP (0.5 mg/ml) adjusted to pH 9.0 by adding 1N sodium hydroxide, was added a 25% aqueous solution of glutaraldehyde so that the final concentration of glutaraldehyde would become 0.05%. The mixed solution was reacted under stirring at room temperature for 22 hours. The resultant solution was then sufficiently dialyzed against a 0.1M phosphate buffer solution (containing 2M urea, pH 7.0) to obtain the toxoid-processed IAP.

(iii) A toxoid-processed reductively methylated IAP was also similarly prepared by using a reductively methylated IAP solution in place of an IAP solution.

Infection prevention test

There were prepared five kinds of the physiological saline solutions containing a dead pertussis vaccine (made by KAKEN PHARMACEUTICAL CO., LTD.), toxoid-processed IAP, toxoid-processed reductively methylated IAP, IAP and reductively methylated IAP, respectively, and 0.1 ml of each of these physiological saline solutions was administered into the peritoneal cavities of the ddY mice (male, 4 weeks old) (13 mice per one group). Two weeks after the administration, the live pertussis 18-323 strain (I-phase) bacteria were inoculated into the encephalon at a rate of $4 \times 10^4$ cells/animal. The life and death of the animals were observed for a period of two weeks after the inoculation to determine the survival rate. The results are shown in Table 5. Used as the control was a group of mice which were treated similarly by giving 0.1 ml of a physiological saline solution alone into the peritoneal cavity.

TABLE 5

1 bil = $10^9$ cells

| Sample | Dose | Number of animals which survived/total number of animals tested | Survival rate (%) |
|---|---|---|---|
| The present invention Reductively methylated IAP | 0.04 μg/animal | 7/13 | 54 |
|  | 0.2 | 6/13 | 46 |
|  | 1 | 9/13 | 69 |
| Toxoid-processed reductively | 0.2 μg/animal | 7/13 | 54 |
|  | 1 | 8/13 | 62 |

TABLE 5-continued

| | 1 bil = 10⁹ cells | | |
|---|---|---|---|
| Sample | Dose | Number of animals which survived/ total number of animals tested | Survival rate (%) |
| methylated IAP Comparative Example | 5 | 11/13 | 85 |
| Dead pertussis vaccine | 0.4 bil/animal | 9/13 | 69 |
| Toxoid processed IAP | 0.2 μg/animal | 7/13 | 54 |
| | 1 | 8/13 | 62 |
| | 5 | 10/13 | 77 |
| IAP | 0.04 μg/animal | 6/13 | 46 |
| | 0.2 | 8/13 | 62 |
| | 1 | 3/13 | 23 |
| Control | 0 | 2/13 | 15 |

As seen from the above table, the reductively methylated IAP showed an effective infection preventive action without toxoid processing with glutaraldehyde. When the reductively methylated IAP was subjected to toxoid processing, it showed a preventive action almost equal to that of the toxoid-processed non-modified IAP.

As described in detail hereinabove, the novel proteinic active substances according to the present invention are very useful in the treatment and prevention of diabetes or in pertussis vaccines The effective dose for human applications varies depending on specific activity of the active substances. Usually, for use in promotion of insulin promoting secretory activity, they are administered within the amount range of 10 ng/kg (body weight) to several ten μg/kg (body weight).

As for the way of administration to the patient, intravenous injection is most effective in every use, but there may as well be employed other modes of administration such as intraperitoneal, intramuscular or subcutaneous injection, direct administration into the digestive organs, or oral, intrarectal, sublingual, nasal mucosal, intra-arterial, intralymphangial or intratracheal administration.

As regards the form of administration, there may be cited injections, suppositories, enteric and gastric coatings, sublingual tablets and inhalants. A most simple example of injection compositions is a 1-ml mixture of 10,000 units of insulin secretory active substance, 9 mg of NaCl and sterile distilled water.

The definition of the activity units used in the present invention is described in Japanese Patent Application Laying Open No. 96392/72 which corresponds to G.B. Patent No. 1,569,046.

It will be apparent to those skilled in the art that other additives having no possibility of affecting the activity of the active substance may be suitably mixed in the preparation of medicaments.

What is claimed is:

1. A biological active substance obtained by reacting Islets-Activating Protein which has been isolated from a culture of a bacterial strain of *Bordetella pertussis* (Phase I or II), which has the following properties:
   (1) a molecular weight of 73,000±11,000 as determined by the gel-filtration method;
   (2) a protein content of not less than 95% by weight as determined by Lowry's method;
   (3) the amino acid composition of the protein moiety thereof (average ratio, μm/100μM), comprising from 7.5 to 7.9 of aspartic acid, from 6.8 to 7.8 of threonine, from 5.9 to 7.6 of serine, from 8.8 to 10.0 of glutamic acid, from 5.5 to 6.4 of proline, from 8.7 to 9.6 glycine, from 9.to 10.8 of alanine, from 1.0 to 2.5 of cystine/2, from 6 to 5 to 7.6 of valine, from 2.5 to 3.3 of methionine, from 3.6 to 4.6 of isoleucine, from 7.4 to 8.7 of leucine, from 5.1 to 6.8 of tyrosine, from 3.7 to 4.5 of phenylalanine, from 3.1 to 4.4 of lysine, from 0.9 to 1.5 of histidine and from 6.1 to 6.6 arginine;
   (4) an isoelectric point of a pH of 8.9±0.5; and
   (5) an optical rotation, $[\alpha]_D^{25}$, of $-29\pm5°$, and which shows (I) a very sharp single band on the cathode side in the disc-electrophoretogram with 7.5% by weight of polyacrylamide gel containing 1N potassium hydroxide-glacial acetic acid buffer solution of a pH of 4.3 and (II) a hydroxyapatite column-chromatographic pattern in which the said protein is eluted with an aqueous 0.1M phosphate buffer solution of a pH of 7.0 containing 0.5M of sodium chloride,
with a carbonyl compound of formula (I):

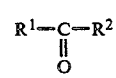

wherein R¹ is a hydrogen atom, a methyl group or a group represented by the formula:

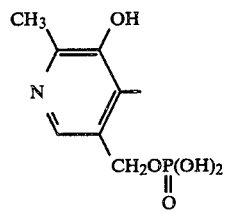

and R² is a hydrogen atom or an alkyl group of 1 to 3 carbon atoms in the presence of a reducing agent.

2. The biologically active substance according to claim 1, wherein said Islets-Activating Protein has free amino group(s).

3. The biologically active substance according to claim 2, wherein said free amino group(s) of the Islets-Activating Protein are modified by said carbonyl compound.

4. The biologically active substance according to claim 3, wherein from 4 to 95 mol % of said free amino groups is modified by said carbonyl compound.

5. The biologically active substance according to claim 1, wherein said reducing agent is selected from the group consisting sodium borohydride, sodium cyanoborohydride, pyridine-borane, morpholine-borane and a complex of an amine and borane.

6. The biologically active substance according to claim 5, wherein said complex of an amine and borane is dimethylamine-borane or triethylamine-borane.

7. An anti-diabetic pharmaceutical composition in unit dosage form, comprising:
    an anti-diabetically active amount of a biologically active substance according to claim 1 and a pharmaceutically acceptable carrier.

8. An anti-pertussis pharmaceutical composition in unit dosage form, comprising:
    a preventively effective amount of a biologically active substance according to claim 1 and a pharmaceutically acceptable carrier.

9. A process for producing a biologically active substance, comprising the step of:
reacting Islets-Activating Protein which has been isolated from the culture of a bacterial strain of *Bordetella pertussis* (Phase I or II) and has the following properties:
(1) a molecular weight of 73,000±11,000 as determined by the gel-filtration method;
(2) a protein content of not less than 95% by weight as determined by Lowry's method;
(3) the amino acid composition of the protein moiety thereof (average ratio, μM/100 μM), comprising from 7.5 to 7.9 of aspartic acid, from 6.8 to 7.8 of threonine, from 5.9 to 7.6 of serine, from 8.8 to 10.0 of glutamic acid, from 5.5 to 6.4 of proline, from 8.7 to 9.6 glycine, from 9.0 to 10.8 of alanine, from 1.0 to 2.5 of cystine/2, from 6.5 to 7.6 of valine, from 2.5 to 3.3 of methionine, from 3.6 to 4.6 of isoleucine, from 7.4 to 8.7 of leucine, from 5.1 to 6.8 of tyrosine, from 3.7 to 4.5 of phenylalanine, from 3.1 to 4.4 of lysine, from 0.9 to 1.5 of histidine and from 6.1 to 6.6 arginine;
(4) an isoelectric point of a pH of 8.9±0.5; and
(5) an optical rotation, $[\alpha]_D^{25}$, of $-29\pm5°$, and which shows (I) a very sharp single band on the cathode side in the disc-electrophoretogram with 7.5% by weight of polyacrylamide gel containing 1N potassium hydroxide-glacial acetic acid buffer solution of a pH of 4.3 and (II) a hydroxyapatite column-chromatographic pattern in which the said protein is eluted with an aqeuous 0.1M phosphate buffer solution of a pH of 7.0 containing 0.5M of sodium chloride,
with a carbonyl compound of formula (I):

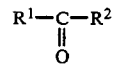

wherein $R^1$ is a hydrogen atom, a methyl group or a group represented by the formula:

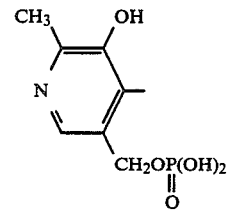

and $R^2$ is a hydrogen atom or an alkyl group of 1 to 3 carbon atoms in the presence of a reducing agent.

10. The process according to claim 9, wherein said reducing agent is a member selected from the group consisting of sodium borohydride, sodium cyanoborohydride, pyridine-borane, morpholine-borane and a complex of an amine and borane.

11. The process according to claim 10, wherein said complex of an amine and borane is dimethylamine-borane or triethylamine-borane.

* * * * *